United States Patent [19]
Land et al.

[11] Patent Number: 5,968,340
[45] Date of Patent: Oct. 19, 1999

[54] POLAROGRAPHIC SELF-REFERENCING PROBE AND METHOD FOR USING

[75] Inventors: Stephen C. Land, Falkirk, United Kingdom; Richard Sanger, Woods Hole; Peter J.S. Smith, Falmouth, both of Mass.

[73] Assignee: Marine Biological Laboratory, Woods Hole, Mass.

[21] Appl. No.: 08/834,902

[22] Filed: Apr. 7, 1997

[51] Int. Cl.$^6$ .................................................. G01N 27/26
[52] U.S. Cl. .......................... 205/775; 204/403; 436/149
[58] Field of Search ............................ 436/149; 204/403; 205/777.5, 775

[56] References Cited

U.S. PATENT DOCUMENTS

| | | | |
|---|---|---|---|
| Re. 31,299 | 7/1983 | Kessler et al. | 204/415 |
| 3,912,614 | 10/1975 | Spracklen et al. | 204/195 B |
| 4,041,933 | 8/1977 | Reichenberger | 128/2 E |
| 4,276,144 | 6/1981 | Hahn et al. | 204/195 P |
| 4,390,405 | 6/1983 | Hahn et al. | 204/415 |
| 4,466,879 | 8/1984 | Ho et al. | 204/415 |
| 4,853,091 | 8/1989 | Mund et al. | 204/1 T |
| 5,393,392 | 2/1995 | Masi | 304/153.16 |

OTHER PUBLICATIONS

Keefe, et al.; "Identification of Calcium Flux in Single Preimplantation Mouse Embryos with the Calcium–Sensitive Vibrating Probe"; (1995); *Biol. Bulletin*, 189: p. 200 Oct./Nov.

Kühtreiber et al.; "Detection of Extracellular Calcium Gradients with a Calcium–Specific Vibrating Electrode"; (1990); *The Jrnl. of Cell Biology*, vol. 110: pp. 1565–1573 Month Unknown.

Land, et al.; "Detection of Extracellular Oxygen Fluxes from Single Cultured Neurons Using a Non–Invasive, Self–Referencing, Oxygen Microelectrode" (1997); *The Faseb Journal*, vol. 11(3): 1 pg. Feb.

Smith; et al.; "the Vibrating Ca$^{2+}$ Electrode: A New Technique for Detecting Plasma Membrane Regions of Ca$^{2+}$ Influx and Efflux"; (1994); *Methods in Cell Biology*, vol. 40: pp. 115–134 Month Unknown.

Smith, J.S.; "Non–Invasive Ion Probes—Tools for Measuring Transmembrane Ion Flux"; (1995); *Nature*, vol. 378: pp. 645–646 Dec.

vom Saal et al.; "Natural History and Mechanisms of Reproductive Aging in Humans, Laboratory Rodents, and Other Selected Vertebrates"; (1994); *The Physiology of Reproduction*, vol. 2: pp. 1213–1314 Month Unknown.

Kochain et al. ("Use of an extracellular, ion–selective, vibrating microelectrode system for the quantification of K+, H+, and Ca2+ fluxes in maize roots and maize suspension cells", Planta (1992) 188:601–610) Month Unknown 1992.

CAPLUS abstract of Lucas et al. ("Biocarbonate ion and hydroxyl ion transport across the plasmalemma of Chara. Spatial resolution obtained using extracellular vibrating probe", Planat (1980), 150(2), 120–31) Month Unknown 1980.

*Primary Examiner*—T. Tung
*Assistant Examiner*—Alex Noguerola
*Attorney, Agent, or Firm*—Hale and Door LLP

[57] ABSTRACT

A polarographic self-referencing probe uses an electrode that is oscillated between two positions. Depending on the electrode used and the voltage applied, the probe can be used to measure oxygen, nitric oxide, or other molecules or compounds.

17 Claims, 6 Drawing Sheets

POLAROGRAPHIC SELF-REFERENCING PROBE AND METHOD FOR USING

STATEMENT OF GOVERNMENT RIGHTS

This invention was made with government funding under grant no. P41-RR01395 from the National Institutes of Health. The government may have certain rights in this invention.

BACKGROUND OF THE INVENTION

This invention relates to polarographic measurement of flux from biological specimens as small as a single cell.

It has been known to use an electrode to polarographically measure oxygen in blood or in tissue samples. As described, for example, in Reissue Pat. No. 31,299, a polarographic oxygen sensor with a reduction electrode and a reference electrode can be used to sense oxygen in samples, such as gases, blood, and tissue. Other oxygen sensors have also been used for measuring dissolved oxygen in such samples.

Other methods have been employed for sensing oxygen for a single cell, but these other approaches typically use highly invasive or intrusive techniques. It would be desirable to be able to measure oxygen and other molecules for specimens as small as a single cell in a non-invasive and non-intrusive manner.

SUMMARY OF THE INVENTION

The system and method of the present invention use a mechanically oscillated self-referencing electrode to measure the flux of molecules, such as oxygen or nitric oxide, from biological samples as small as a single cell in a non-intrusive and non-invasive manner. A controlled voltage is applied to a metal tip on a probe to reduce a molecule, such as oxygen, and thereby to generate a current that is proportional to a difference in the concentration of the molecule. The probe is moved between two positions with a movement like a square wave, and measurements are made at the extreme positions of the movement.

According to the present invention, the flux of oxygen can accurately be measured to or from a single cell, and has been measured in endothelial cells as small as six microns, and other larger cells. The flux of other molecules, such as nitric oxide, ascorbic acid, and insulin, can also be measured from single cells, using similar techniques to those used for oxygen, but are tailored to the appropriate molecule. Other features and advantages will become apparent from the following detailed description, drawings, and claims.

DETAILED DESCRIPTION

Figure 1:
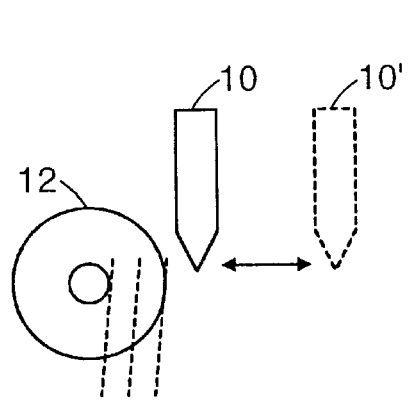
FIG. 1 is a side view of an electrode and a cell according to the present invention.

Referring to FIG. 1, a self-referencing, polarographic electrode 10 can reliably and accurately measure, from a single cell 12, local oxygen influxes generated by respiration and local oxygen effluxes generated by photosynthesis. The flux is measured non-invasively and non-intrusively with a sensitivity that is minimally in the range of high picomole per $cm^2$ per second of oxygen flux. Electrode 10, shown within an oxygen gradient surrounding a respiring cell, is moved slowly (e.g., 0.3–0.75 Hz) between the position shown and a position 10' further from the cell. The movement approximates a square wave, and data is recorded at the end of each movement.

Figure 2:
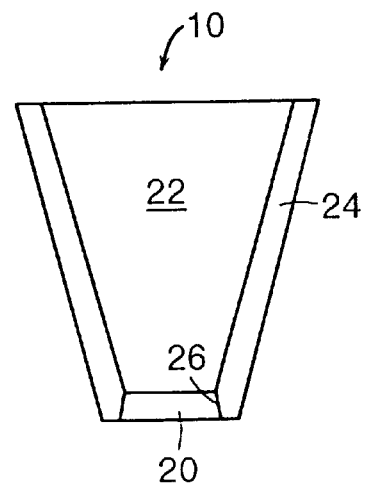
FIG. 2 is a cross-sectional view of the electrode of FIG. 1.

Referring to FIG. 2, electrode 10 may be a Whelan-style, membrane tipped, oxygen microelectrode, such as a commercially available model 723, from Diamond General Development Corp. of Ann Arbor, Mich. Electrode 10 has a tip diameter of approximately 3 μm and is tipped with a gas permeable polymer membrane 20. The electrode has a platinum shaft 22 encased in a glass housing 24. Between the lower end of the platinum shaft and the polymer membrane is a gold reducing surface 26 with a thickness of 1 micron.

Quantitative determinations of chemical concentrations can be made using reduction and/or oxidation reactions, such that the gold surface of the electrode forms a surface for reaction. Using the principle of oxygen reduction under an applied voltage, measurements of oxygen gradients around single cells in culture have successfully been made.

The basis for detecting very low oxygen fluxes is an oxygen reduction reaction that takes place at a gold reaction surface. This reaction can be summarized as follows:

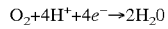

$$O_2 + 4H^+ + 4e^- \rightarrow 2H_2O$$

It has been found that this reduction occurs at an optimal voltage of −0.75 V. The reduction of each $O_2$ molecule by $4e^-$ provides a current flow that is proportional to the concentration of oxygen. To enhance its selectivity for dissolved oxygen, a membrane that is semipermeable to oxygen and water vapor is placed in front of the reactive electrode surface to generate a field of diffusion for oxygen into the electrode.

Figure 3:
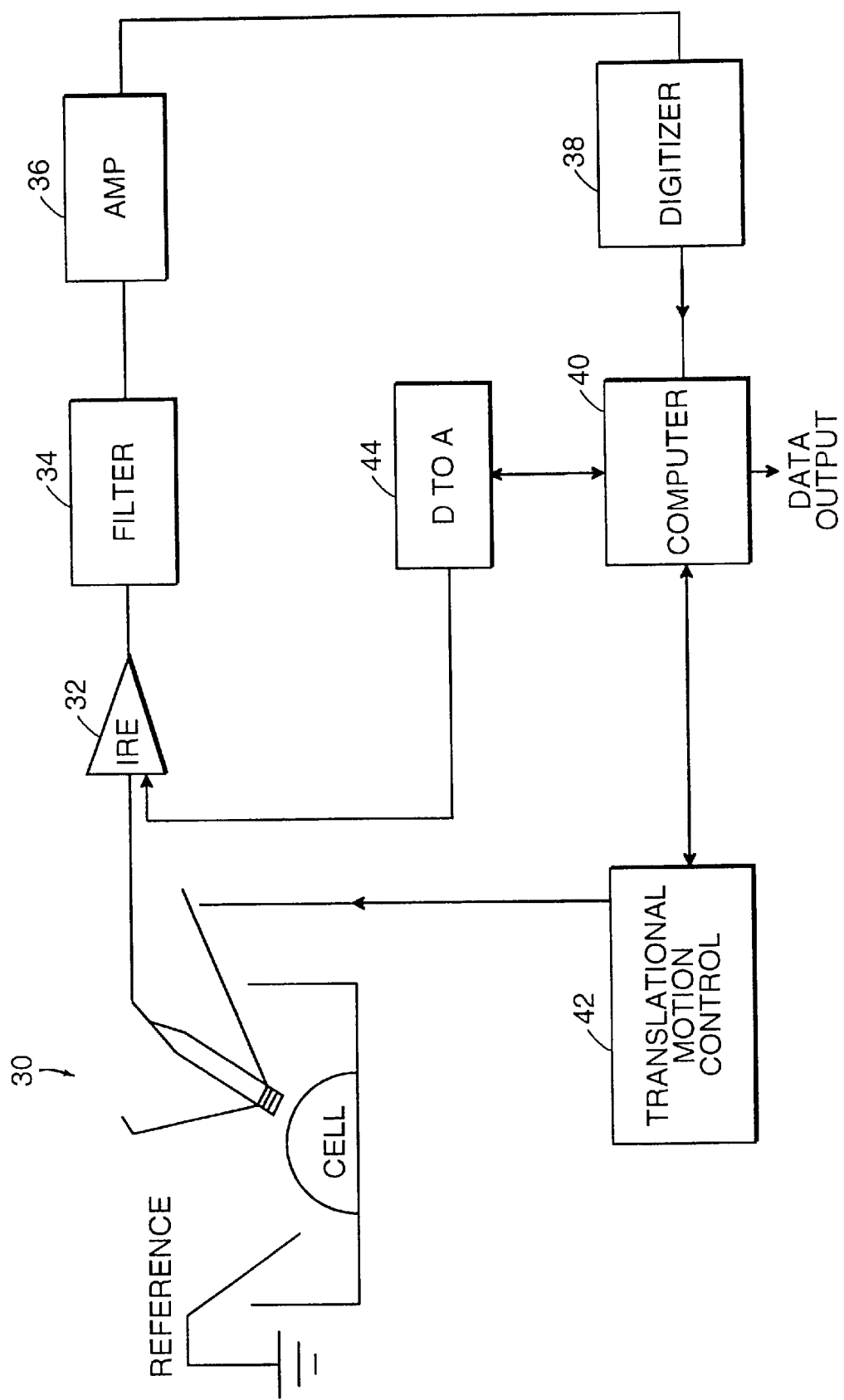
FIG. 3 is a block diagram of circuitry for an embodiment of the present invention.

Referring to FIG. 3, a voltage (such as −0.75 V) is provided to a probe 30 so that oxygen (or some other desired molecule or compound) undergoes a chemical change to generate a current. Probe 30 is electrically connected at the blunt non-sensing end to a current-to-voltage converter 32. Converter 32 is offset with the polarization voltage via a digital-to-analog (D/A) converter 44 so that the probe's voltage potential is the same as the polarization voltage. The resultant voltage is then provided to a filter 34, amplifier 36, and digitizer 38 to filter, amplify, and digitize the converted voltage signal. The resulting digitized signal is provided to a computer 40 that calculates the difference in magnitude of the signal. Such computations are performed on the oscillated probe at each of its positions. This calculated difference can then be readily converted to a flux by knowing the diffusion constant of oxygen.

The same principle can be extended to other dissolved gases or molecules where a selectivity can be obtained at the electrode surface and/or where there is a characteristic redox potential signature.

The system also includes a translational motion control device 42 for slowly oscillating the electrode. This mechanism is similar to those used for positioning an ion-selective probes to sense ions, such as calcium, as described, for example, in Smith et al., "The Vibrating $Ca^{2+}$ Electrode: A New Technique For Detecting Plasma Membrane Regions of $Ca^{2+}$ Influx and Efflux," *Methods in Cell Biology*, Vol. 40, 1994, which is expressly incorporated by reference for all purposes.

The performance of the electrode is subject to variations in the characteristics of the membrane at the tip, i.e., its thickness, width, and resistance. Consequently, each electrode should be characterized prior to use. Such characterization can be achieved by placing the electrode in a standardized air-equilibrated biological saline and plotting current as a function of the voltage applied. The resulting curve typically has a plateau in current at about 60 pA between applied voltages of −0.45 V and −0.8 V, representing a range over which oxygen consumption by the electrode proceeds by the 4e− reduction reaction. The ideal operating voltage rests along this plateau; to maximize signal to noise, −0.75 V was selected as the operational polarizing voltage. Under these conditions, the electrodes have a 90% response time to an oxygen signal in less than four seconds.

Calibration in terms of oxygen concentration (molarity) at the electrode surface requires that the active cathode area, thickness, and permeability coefficients of the membrane be known. In practice, these factors cannot be accurately determined since the membrane characteristics vary with time, temperature, and composition of the medium. Furthermore, because $O_2$ concentration can vary independently of fugacity, subsequent measurements of oxygen concentration through the above relationship are subject to an indeterminate error. Therefore, conversion of the percentage of $O_2$ saturation to $O_2$ concentration in double distilled water is achieved through a conversion table as is known.

The total oxygen flux into a respiring cell (i.e., Q, measured as nanomol per $cm^3$ per second) is a function of the magnitude of an extracellular oxygen gradient and the surface area to volume ratio of the cell. Assuming a spherical geometry and homogeneous mitochondrial distribution, a radial version of the Fick Equation can be derived as follows:

$$\Delta C = (Q \cdot \Delta r \cdot r)/(3D),$$

where $\Delta C$ is the change in concentration (moles) between the translational points $\Delta r$ (cm) apart. Q is the oxygen consumption (nanomole$\cdot cm^{-3} \cdot s^{-1}$), r is the radius of the cell, and the oxygen diffusion constant, D, is $2.5 \times 10^{-5}$ $cm^2$/sec. The probe system of the present invention uses this principle to enable calculation of flux rates by measuring the difference between the oxygen-associated current ($\Delta pA$) at each maxima of displacement. Conversion of $\Delta pA$ into oxygen concentration over the preset translational distance ($\Delta r$) provides a measure of the oxygen gradient which is converted into a real-time measure of flux by multiplication with the diffusion constant for oxygen.

As the electrode is moved between its two positions, time at each extreme must be sufficient for the surrounding oxygen concentration to establish itself at the reaction surface. This time is empirically assessed by experimentation and balanced against the need to minimize the impact of electrode drift. In practice, the time spent at each position is set to be approximately 1.5 seconds. This value will vary with the diffusion characteristics of the sensed gases or molecules.

Because the plasma membrane is a minimal barrier to oxygen diffusion, the magnitude and distribution of the oxygen gradient around a cell is a function of (i) the metabolic status of the cell, (ii) the distribution of mitochondria within the cell, and (iii) the partial pressure of oxygen in the surrounding medium. Therefore, when corrected for external oxygen concentrations, measured oxygen flux within a gradient around a cell constitutes a direct measure of mitochondrial oxidation. The measured oxygen signals can be converted to a measure of flux by substituting the amplified signal into a radial Fick equation.

A distance that the electrode is translated depends on the size of the oxygen gradient around the cell. At each end point of translation, a number of data points are collected, averaged over a short time-frame, and compared with similarly treated data at the alternate end point of displacement.

The concepts used in the self-referencing polarographic oxygen probe of the present invention can also be applied to a system for measuring nitric oxide gradients, and with changes to the reactive surface, for organic molecules and metallic ions. Selective measurement of a nitric oxide signal is similar to that for polarographic oxygen sensing. The signal for measuring nitric oxide is easily distinguished from a signal for measuring oxygen because a positive voltage is applied at the sensor tip for nitric oxide. Under positive voltages there is a plateau in current at 200 pA for a range of applied voltages; within this range, an applied voltage of about +0.8 V has been selected. With this input, the reaction proceeds at the sensing anode as follows:

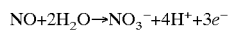

$$NO + 2H_2O \rightarrow NO_3^- + 4H^+ + 3e^-$$

Figure 4:
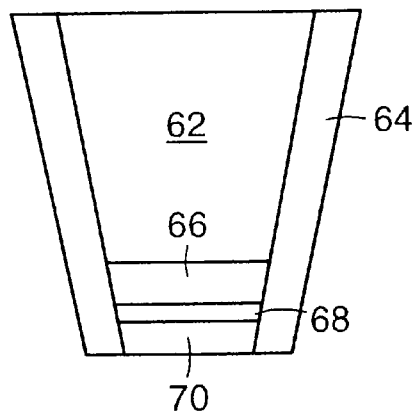
FIG. 4 is a cross-sectional view of an electrode according to another embodiment of the present invention.

Referring to FIG. 4, an electrode 60, such as a model ISO-NOP30 made by World Precision Instruments, Inc. of Sarasota, Fla., can be used. Other suitable designs can also be used, such as the design described in Ichimori et al. (1994) "Practical Nitric Oxide Measurement Employing a Nitric Oxide-Selective Electrode," Rev. Sci. Instruments 65(8): 2714–2718. In the ISO-NOP30, a platinum wire 62 with a tip diameter of about 1–5 microns is etched and encased in a glass case 64. Platinum exposed at the tip is covered by three membranes: an innermost electrodeposited KCl layer 66, a membrane 68 with an NO-selective resin, and a polymer membrane 70 as the outermost one. Each membrane is approximately 1 $\mu$m in thickness. KCl layer 66 functions as a conductor during NO oxidation. An NO-selective resin can consist of a nitrocellulose solution prepared by diluting 25% "Colloidion" (available from Wako Chem Co.) with a 3:1 mix of diethylether/ethanol. The membrane is applied under a vacuum. A non-selective, gas permeable membrane is applied, once again by vacuum, which insulates the platinum surface from dissolved ion and electrochemical interactions. A reference cathode consists of a carbon fiber rod.

Generating a voltage to activate the NO-probe and subsequent sensing of the current signal may be achieved using hardware similar to that described above with FIG. 3, with a difference being that a positive voltage is applied to generate a picoamp current. Conceptually, large increases in sensitivity would be expected for the same reasons demonstrated above for oxygen.

EXAMPLES

Figure 5:
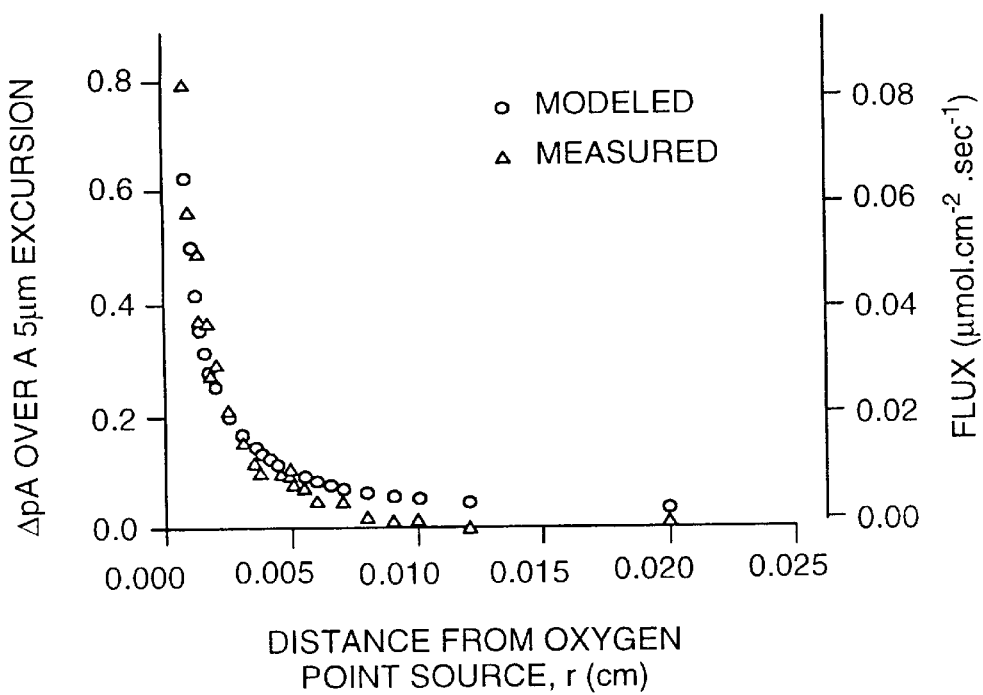
FIGS. 5 and 6 are graphs illustrating measured data versus modelled data.
Figure 6:
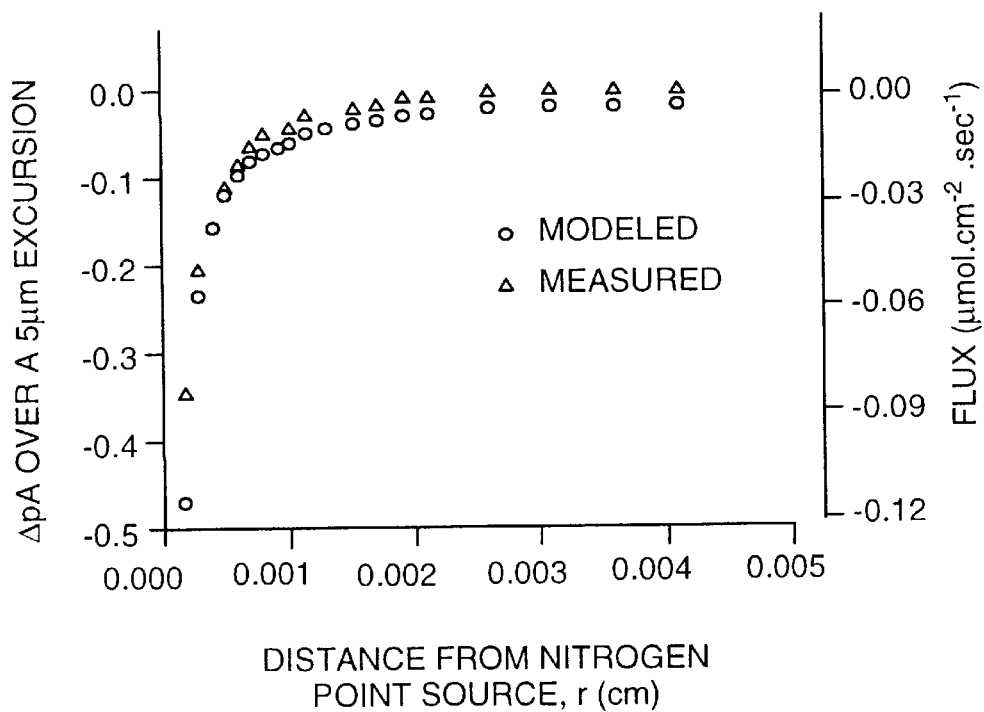

Referring to FIGS. 5 and 6, tests were performed to compare measured and modeled data. A point source with a tip diameter of 3 $\mu$m containing gaseous $N_2$ or $O_2$ was used to construct an artificial oxygen diffusion gradient in water. Point sources containing $N_2$ create an apparent inward diffusion field of oxygen towards the tip as $N_2$ partially displaces $O_2$ from the medium nearby. Point sources containing $O_2$ will generate an outward diffusion field of oxygen. Artificial gradients established in this way are stable after an equilibration period of 1 hour.

Static and oscillating measurements were taken at known distances away from the tip of the source pipette. The current differences in picoamperes, $\Delta pA$, were measured at each sampling point by oscillating the electrode over an excursion of 5 $\mu$m at a frequency of 0.3 Hz. The measured oxygen concentration difference over the excursion distance was then calculated from the relationship $\Delta pA=S(\Delta C/Cb)/2.3$, where S is the slope of the calibration curve for the oxygen electrode ($\mu mol.cm^{-3}.pA^{-1}$), $\Delta C$ is the difference in oxygen concentration, and Cb is the background concentration of oxygen in the medium ($\mu mol.cm^{-3}$). Flux ($\mu mol.cm^{-2}.sec^{-1}$) was then calculated by substituting $\Delta C$. $\Delta C$ into the Fick equation as $J=-D(\Delta C/\Delta r)$, where D is the diffusion coefficient for oxygen ($2.5\times10^{-5}cm^2.sec^{-1}$), and $\Delta r$ is the excursion distance (cm).

Static measurements of oxygen concentration at each sampling point were converted to a current differential for a 5 $\mu$m excursion by applying the polarographic data to a voltage model previously derived in the incorporated Smith et al. article, noted above, for artificial sources developed to generate ion gradients. The version used here was:

$$\Delta pA=S[(-K\Delta r)/(Cb.r^2+Kr)]/2.3$$

where r (cm) is the radius away from the artificial point source and K (micromol.cm$^{-2}$) is an empirically derived constant that describes the slope of the oxygen diffusion curve away from the point source. The $\Delta pA$ derived from the model can then be used to calculate C and oxygen flux as described above for the measured data.

FIG. 5 shows the fit between modeled and measured $\Delta pA$ and flux obtained from an artificially generated oxygen diffusion field; and FIG. 6 shows the fit between modeled and measured $\Delta pA$ and flux obtained from an artificially generated $N_2$ diffusion field where $O_2$ is displaced from the tip of the electrode by $N_2$. Note that the design and operating voltage of the oxygen electrode precludes measurement of $N_2$ or its oxidated forms.

Figure 7:
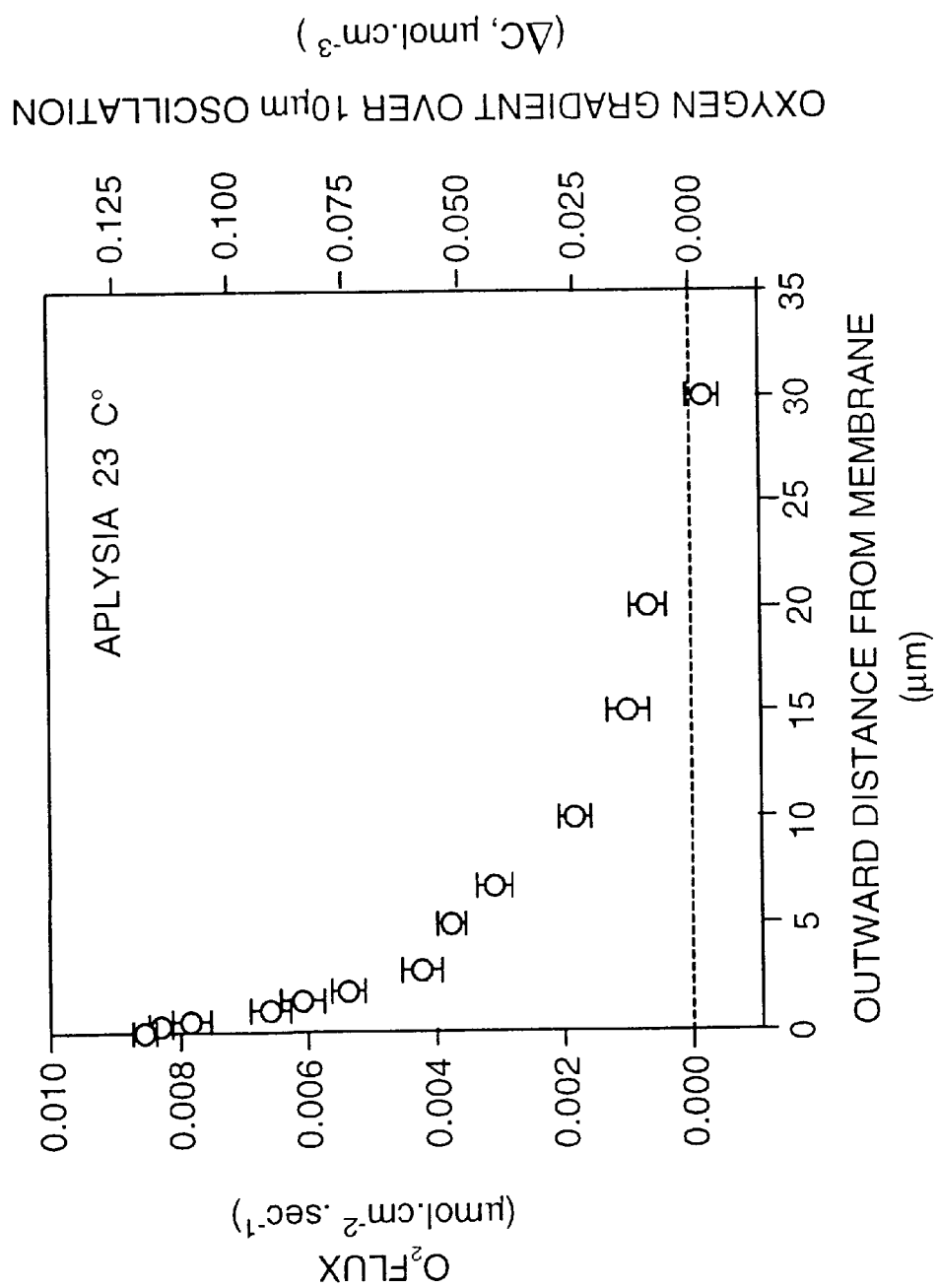
FIGS. 7–10 are graphs illustrating measurements of flux made with the probe of the present invention.
Figure 8:
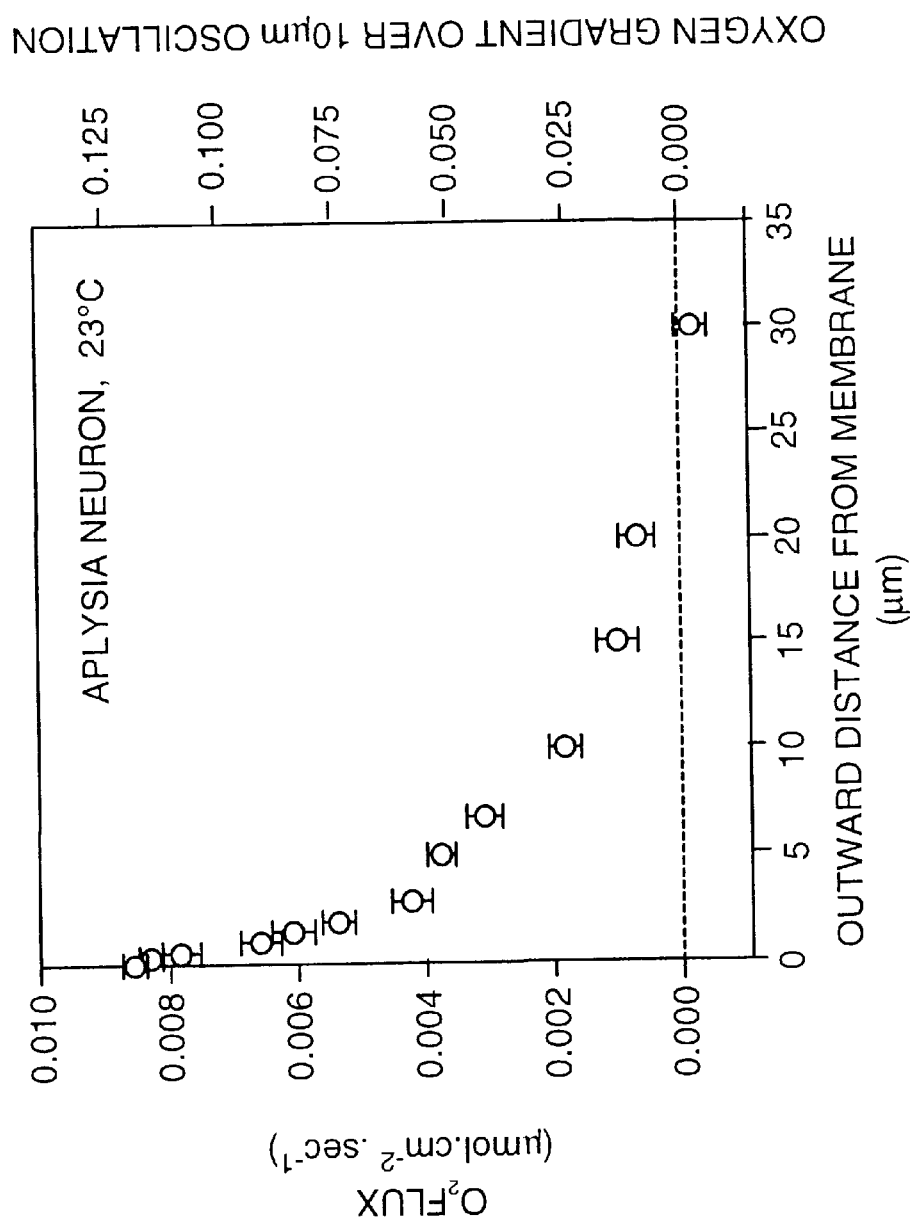

In another example, data collected from a single isolated Aplysia cell and Aplysia neuron are shown in FIGS. 7 and 8, respectively. The cell was maintained in artificial seawater equilibrated with air. The oxygen flux was measured with an electrode such as that shown in FIG. 2 towards a sink (influx), so the flux signal showed positive polarity. The electrode was vibrated with a 0.3 Hz frequency with an amplitude of 5 microns. Flux measurements taken less than 10 microns from the cell membrane showed a significant signal in the high nanomole per $\mu m^2$ per second relative to measures taken 500 $\mu$m away.

Figure 9:
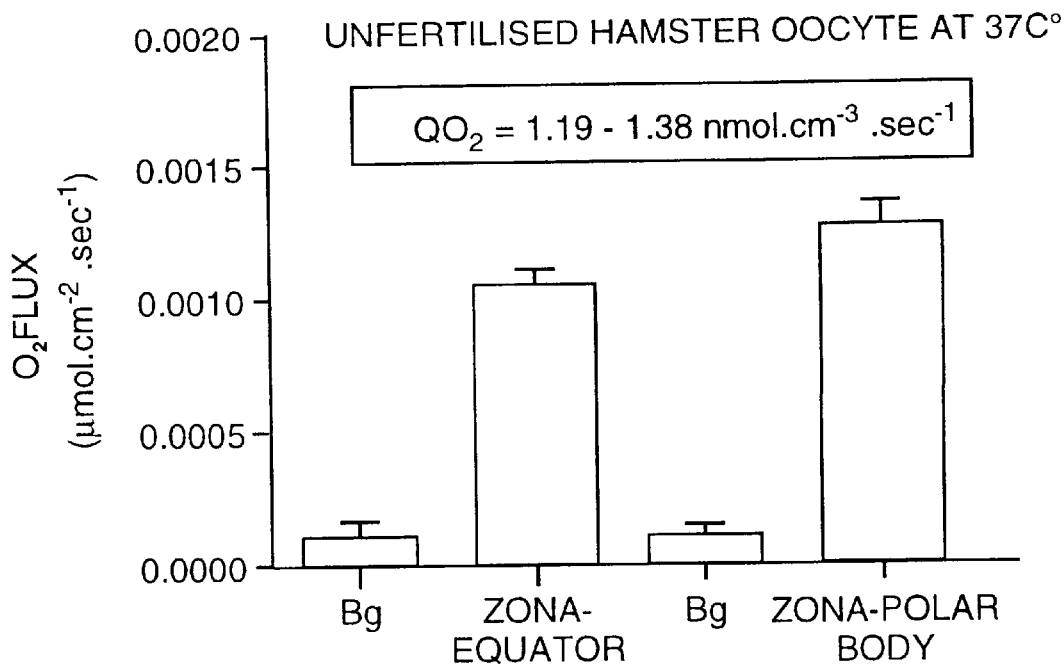

FIG. 9 shows data from another example in which oxygen flux from an unfertilized hamster oocyte at 37° C. was measured. The term zona-equator refers to measures taken at the mid-point of the equator of the oocyte; zona-polar body refers to measures taken at the closest approach to the polar body; and Bg is a background measure taken 100 microns from the oocyte. Each point represents a mean +/-SEM of 100 data points at each position. The excursion was at 5 microns with a frequency of 0.3 Hz. The $QO_2$ was calculated from the radial Fick equation noted above.

Figure 10:
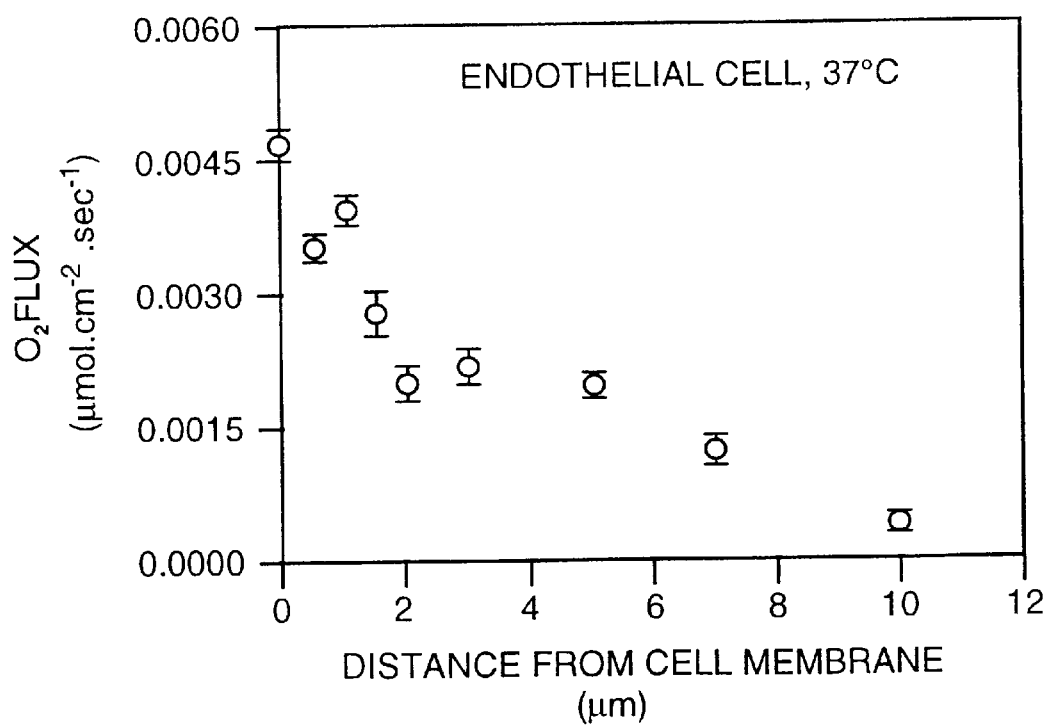

FIG. 10 illustrates the oxygen flux that was measured from an endothelial cell at 37° C. The electrode had an excursion distance of 5 microns with a frequency at 0.3 Hz; and values are means +/-SEM of 50 data points collected at each position.

Having described an embodiment of the present invention, it should be apparent that modifications can be made without departing from the scope of the present invention. Note that other probes can be used to measure other molecules and compounds, such as ascorbic acid and insulin, using a translated, self-referencing, polarographic approach.

What is claimed is:

1. A method for sensing a molecule from a biological specimen, the method comprising the steps of:

oscillating an electrode between first and second positions near the specimen;

applying a voltage to a portion of the electrode so that the molecule to be sensed undergoes a chemical change to generate a position dependent current; and sensing the current at the first and second positions and using the sensed current to determine a flux of the molecule with respect to the specimen.

2. The method of claim 1, wherein the probe is used to sense oxygen flux, and wherein the applying step includes applying a negative voltage.

3. The method of claim 1, wherein the probe is used to sense nitric oxide flux, and wherein the applying step includes applying a positive voltage.

4. The method of claim 1, wherein the probe is used to sense insulin flux.

5. The method of claim 1, wherein the probe is used to sense ascorbic acid flux.

6. The method of claim 1, wherein the sensing step includes providing the current to a current-to-voltage converter and digitizing the voltage.

7. The method of claim 1, wherein the oscillating step includes moving the electrode at a frequency in the range of about 0.3 Hz to 0.75 Hz.

8. The method of claim 1, wherein the specimen is a single cell, the oscillating step including oscillating the electrode between first and second positions near a single cell, and the sensing step including determining a flux of the molecule with respect to a single cell.

9. The method of claim 8, wherein the probe is used to sense oxygen flux for a single cell, and wherein the applying step includes applying a negative voltage.

10. The method of claim 8, wherein the probe is used to sense nitric oxide flux for a single cell, and wherein the applying step includes applying a positive voltage.

11. The method of claim 8, wherein the sensing step includes providing the current to a current-to-voltage converter and digitizing the voltage.

12. The method of claim 8, wherein the oscillating step includes moving the electrode at a frequency in the range of about 0.3 Hz to 0.75 Hz.

13. A system for sensing a molecule from a biological specimen, the system comprising:

an electrode;

a translational mechanism for moving the electrode between at least two positions;

a voltage source for applying a voltage to a portion of the electrode at each of the two positions, wherein the molecule to be sensed undergoes a chemical change upon application of said voltage; and circuitry for sensing a current from the electrode in response to the applied voltage at each position and for converting the sensed current to a measurement of flux of the molecule.

14. The system of claim 13, wherein the electrode has a surface for reducing oxygen in response to a negative voltage.

15. The system of claim 13, wherein the electrode has a surface for reducing nitric oxide in response to a positive voltage.

16. The system of claim 13, wherein the sensing circuitry includes a current-to-voltage converter, signal processing circuitry, and a computer.

17. The system of claim 16, wherein the computer provides to the current-to-voltage converter a voltage used to polarize the electrode.

* * * * *